(12) United States Patent
Meacham et al.

(10) Patent No.: US 9,725,709 B2
(45) Date of Patent: Aug. 8, 2017

(54) INTRACELLULAR DELIVERY AND TRANSFECTION METHODS AND DEVICES

(71) Applicant: OpenCell Technologies, Inc., Atlanta, GA (US)

(72) Inventors: John Mark Meacham, Saint Louis, MO (US); Kiranmai Durvasula, Duluth, GA (US); Andrei G. Fedorov, Atlanta, GA (US); Fahrettin Levent Degertekin, Atlanta, GA (US); Akash Mehta, Atlanta, GA (US)

(73) Assignee: OPENCELL TECHNOLOGIES, INC., St. Louis, MO (US)

( * ) Notice: Subject to any disclaimer, the term of this patent is extended or adjusted under 35 U.S.C. 154(b) by 338 days.

(21) Appl. No.: 14/205,948

(22) Filed: Mar. 12, 2014

(65) Prior Publication Data

US 2014/0273229 A1    Sep. 18, 2014

Related U.S. Application Data

(60) Provisional application No. 61/777,980, filed on Mar. 12, 2013.

(51) Int. Cl.
*C12N 15/87* (2006.01)
*C12N 13/00* (2006.01)

(52) U.S. Cl.
CPC ............. *C12N 13/00* (2013.01); *C12N 15/87* (2013.01)

(58) Field of Classification Search
None
See application file for complete search history.

(56) References Cited

U.S. PATENT DOCUMENTS

2010/0160183 A1* 6/2010 Xu .................... C12N 15/63
506/30

* cited by examiner

*Primary Examiner* — Jim Ketter
(74) *Attorney, Agent, or Firm* — Thomas Horstemeyer, LLP (57) ABSTRACT

Embodiments of the present disclosure provide a multistage procedure for treatment of biological samples (e.g., living cells with membranes, and the like) with a substance (e.g., a drug, DNA, RNA, plasmids, and other biomolecules or materials) to achieve more efficacious intracellular delivery and transfection.

17 Claims, 6 Drawing Sheets

1. Steps 1 and 2 performed in one chamber
2. Cells and substances present for both steps.

Step 1: electroporation

Step 2: electrophoresis   Step 2: magnetophoresis   Step 2: acoustophoresis Step 1: mechanoporation Step 2: electrophoresis   Step 2: magnetophoresis   Step 2: acoustophoresis Step 1: thermoporation Step 2: electrophoresis   Step 2: magnetophoresis   Step 2: acoustophoresis

FIG. 7

INTRACELLULAR DELIVERY AND TRANSFECTION METHODS AND DEVICES

CLAIM OF PRIORITY TO RELATED APPLICATION

This application claims priority to U.S. provisional application entitled "CELL TRANSFECTION METHODS AND DEVICES" having Ser. No. 61/777,980, filed on Mar. 12, 2013, which is entirely incorporated herein by reference.

STATEMENT OF GOVERNMENTAL SUPPORT

This invention was made with government support under contract 2R44RR02571302, awarded by the National Institute of Health (NIH). The government has certain rights in the invention.

BACKGROUND

Delivery of small and macromolecules—including DNA, drug molecules, imaging agents, peptides, antibodies, and enzymes—into cells is critical to realizing their full potential in a range of research and therapeutic applications; yet, intracellular delivery and transfection remain difficult tasks. In particular, effective transfection is typically the most important, and potentially limiting, step in numerous molecular biology and genetic modification protocols. In order to achieve a desired outcome, cargo molecules must reach a specific intracellular target (e.g., the nuclear or mitochondrial genomes for gene therapy).

Approaches to intracellular delivery are categorized as: (1) those that use biological/viral vectors and (2) those that rely on non-viral chemical vectors or physical techniques (application of an energy field) to access the cell interior or specific organelles (including the nucleus). While multiple barriers to effective nuclear delivery of DNA exist (e.g., the extracellular matrix, cell membrane, cytoplasm, and nuclear envelope), conventional physical transfection solutions like sonoporation, laserfection, and electroporation focus only on permeabilization of the cell membrane and not on transport of DNA. As a result, current techniques are not as effective as desired, and there is a need to overcome deficiencies in current techniques.

SUMMARY

Embodiments of the present disclosure provide a multi-stage procedure for treatment of biological samples (e.g., living cells with membranes, and the like) with a substance (e.g., a drug, DNA, RNA, plasmids, and other biomolecules or materials) to achieve more efficacious intracellular delivery and transfection.

In an embodiment, a method of delivering a substance into a living cell having a cell membrane, among others, includes: a) permeabilization of the cell membrane in a suspension, and b) insertion of a substance into the cell interior through pores formed during permeabilization of the membrane. In an embodiment, steps a) and b) are performed sequentially in a single chamber or steps a) and b) are performed separately. In an embodiment, permeabilization includes permeabilization of the cell membrane using a technique selected from: mechanical poration, electrical poration, thermal poration, and a combination of two or more of these techniques. In an embodiment, the insertion is conducted using an energetic technique selected from: an electrophoretic technique, a magnetophoretic technique, an acoustophoretic technique, and a combination of two or more of these techniques. In an embodiment, the substance is selected from: a charged substance, a magnetic substance, a substance that moves under the action of an acoustic field, and a combination of two or more of these.

Other devices, methods, features, and advantages will be, or become, apparent to one with skill in the art upon examination of the following drawings and detailed descriptions. It is intended that all such additional compositions, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure.

FIG. 5A illustrates a SEM image of porated HEK293 cells (adherent, about 15 µm diameter) following STEAM treatment. FIG. 5B illustrates a comparison of biomolecule delivery into HEK293 cells by STEAM (closed bars/symbols, solid lines) and commercial electroporation (open bars/symbols, dashed lines) including fluorescence microscopy after delivery of the largest molecule (2 MDa FITC-labeled dextran). FIG. 5C illustrates a similar comparison as shown in FIG. 5B of a biomolecule delivery into Jurkat cells (suspension, about 12 µm diameter). FIG. 5D is a graph that illustrates the delivery efficiency vs. cargo molecule size for STEAM treatment of primary monocytes. Manufacturer recommended protocols were used to obtain electroporation results with an Eppendorf Muliporator.

FIG. 6A illustrates a schematic showing a prototype cartridge for combined mode treatment with illustration of mechanoporation/electrophoresis process. FIG. 6B illustrates the transfection of HEK293 cells (2 MM/ml) with GFP expressing plasmid (pmaxGFP, µ50 g/ml) 24 hours after STEAM treatment. FIG. 6C illustrates the transfection of HEK293 24 hours after STEAM treatment and application of 75 V/cm field for 500 µs.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biochemistry, biology, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion:

Embodiments of the present disclosure provide a multistage procedure for treatment of biological samples (e.g., living cells with membranes, and the like) with a substance (e.g., a drug, DNA, RNA, plasmids, and other biomolecules or materials) to achieve more efficacious intracellular delivery and transfection. In an embodiment, the method includes application of an energy field (e.g., electric, mechanical, electromechanical, and thermal, among others) for cell membrane permeabilization (or permeabilization of cell like structures such as a virus, a virus like particle, a vesicle, and other nano- and microstructures defined by a membrane) followed by driving and inserting substances (e.g., molecules, charged molecules, and the like such as DNA, RNA, or other biological material or molecules) to and into the porated cells through the resultant pores. In an embodiment, method accomplishes the permeation in one step and in a separate step accomplishes driving and inserting substances into the cell.

Embodiments of the present disclosure are suited for intracellular delivery and transfection for many research and therapeutic applications, including pharmaceutical, biotech, bioproduction, and clinical applications, among others. In particular, embodiments of the present disclosure have been demonstrated in the laboratory using fluorescent markers, DNA plasmids encoding fluorescent proteins (to demonstrate transfection), and in a number of mammalian cell types. Although cells are mentioned throughout the description, in each appropriate instance, a cell can be replaced with a cell like structure.

An advantage of embodiments of the present disclosure includes overcoming one or more barriers to effective transfection through application of multiple physical fields, simultaneously and sequentially. Active transport of substances after membrane poration ensures a more even distribution and higher concentration of substances within the cytoplasm providing a greater opportunity for them to reach a specific intracellular target and to achieve a desired outcome, which is a more effective sequence of steps as compared to driving the materials to the cell membrane or exterior surface and then porating the membrane or using a single step to accomplish poration and transport.

One embodiment of the present disclosure provides a means of cell membrane permeabilization and active transport of charged molecules (such as DNA, RNA, and the like) to and into the cell interior through the resultant pores. This embodiment can include the incorporation of a reservoir for electrical treatment of biological samples (e.g., cells, DNA, RNA, plasmids, and other biomolecules or materials) after processing by an electrosonic droplet generator (termed "Electrosonic Cell Manipulation Device" among other descriptions), which is the subject of U.S. Pat. Nos. 7,312,440; 7,714,274; 7,208,727; 7,557,342; 7,989,763; and 7,704,743, each of which is incorporated herein by reference. The electrosonic cell manipulation device represents systems and methods for injecting substances into living cells having membranes, sorting cells, extracting materials from cells, and manipulating cells through application of energy fields. In an embodiment, the purpose of the additional reservoir is to apply an electric field for electrophoresis of molecules such as DNA or other biological material to and into permeabilized cells, both (cells and materials) of which are suspended in the sample mixture within the additional reservoir. In an embodiment, the molecules can be added separately.

Both electroporation and sonoporation rely on physical forces to realize a temporary increase in cell membrane permeability (e.g., by exceeding a threshold transmembrane voltage or threshold mechanical deformation of the cell); however, electroporation often results in more efficient delivery of DNA. While the exact mechanisms of DNA transport across the cell membrane are not known, a closer investigation of typical experimental conditions under which gene electrotransfer is performed provides a basis for the improvement in performance. DNA is a large and highly-charged molecule. Electroporation (and subsequent nuclear insertion to achieve transfection) is performed using long millisecond square or exponentially decaying pulses. These voltage signal waveforms provide not only a mechanism for membrane permeabilization but also a means for electrophoretic movement of the charged DNA throughout the duration of the pulse. Indeed, it has been suggested that optimum gene electrotransfer might be achieved through a combination of short high-voltage (HV) and long low-voltage (LV) pulses [Kanduser, M., Miklavcic, D., and Pavlin, M., 2009, "Mechanisms involved in gene electrotransfer using high- and low-voltage pulses—an in vitro study," Bioelectrochemistry, 74(2), pp. 265-271; Pavlin, M., Flisar, K., and Kanduser, M., 2010, "The role of electrophoresis in gene electrotransfer," Journal of Membrane Biology, 236(1), pp. 75-79]. Short HV pulses are needed for permeabilization, while longer LV pulses electrophoretically drag DNA to and into the cell.

Mechanical destabilization of the cell membrane provides no such means for active transport of genes to and into the cell (electrophoretic or otherwise). For this reason, sonoporation and other mechanical gene transfer techniques rely on diffusion as the means of DNA transport. Diffusion of DNA (and specifically large DNA molecules) into the cell may not occur before pores are able to reseal eliminating the potential for successful transfection [Meacham, J. M., Durvasula, K., Degertekin, F. L., and Fedorov, A. G., 2013, "Physical Methods for Intracellular Delivery: Practical Aspects from Laboratory Use to Industrial-Scale Processing," Journal of Laboratory Automation, Online First Jun. 27, 2013; Krassowska, W., and Filev, P. D., 2007, "Modeling electroporation in a single cell," Biophysical Journal, 92(2), pp. 404-417; Lechardeur, D., Verkman, A. S., and Lukacs, G. L., 2005, "Intracellular routing of plasmid DNA during non-viral gene transfer," Advanced Drug Delivery Reviews, 57(5), pp. 755-767.]. Further, even if DNA is able to enter the cell, DNA transport by diffusion to the nucleus may not occur before the DNA degrades in the cytoplasm.

Decoupling of the permeabilization and electrophoresis into discrete steps (as opposed to electroporation) allows one to use a more preferred method of cell membrane permeabilization (step 1) while actively inserting the substance (e.g., DNA) under a reduced amplitude electric field (step 2), thus avoiding potentially destructive treatment by the high electric fields required for electroporation. In this way, effective transfection may be achieved with lower cell mortality. Thus, embodiments of the present disclosure can provide superior performance relative to currently used techniques.

In general, embodiments of the present disclosure, which provides a multistage procedure for treatment of biological samples, are capable of independently (stage/step 1) permeabilizing the membranes of living cells and (stage/step 2) then driving charged molecules and other biological materials to and into cells. Treated cells can then be further processed, plated, cultured, and/or analyzed to assess desired treatment outcomes.

Figure 1:
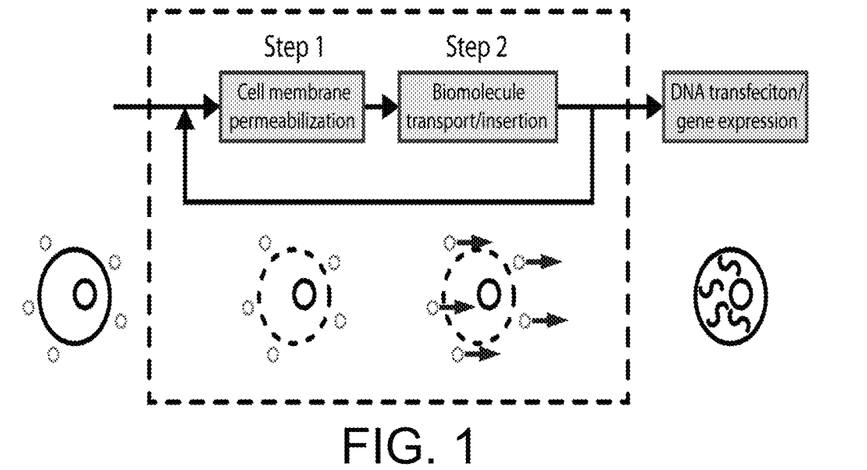
FIG. 1 illustrates a multi-stage cell transfection method.
Figure 7:
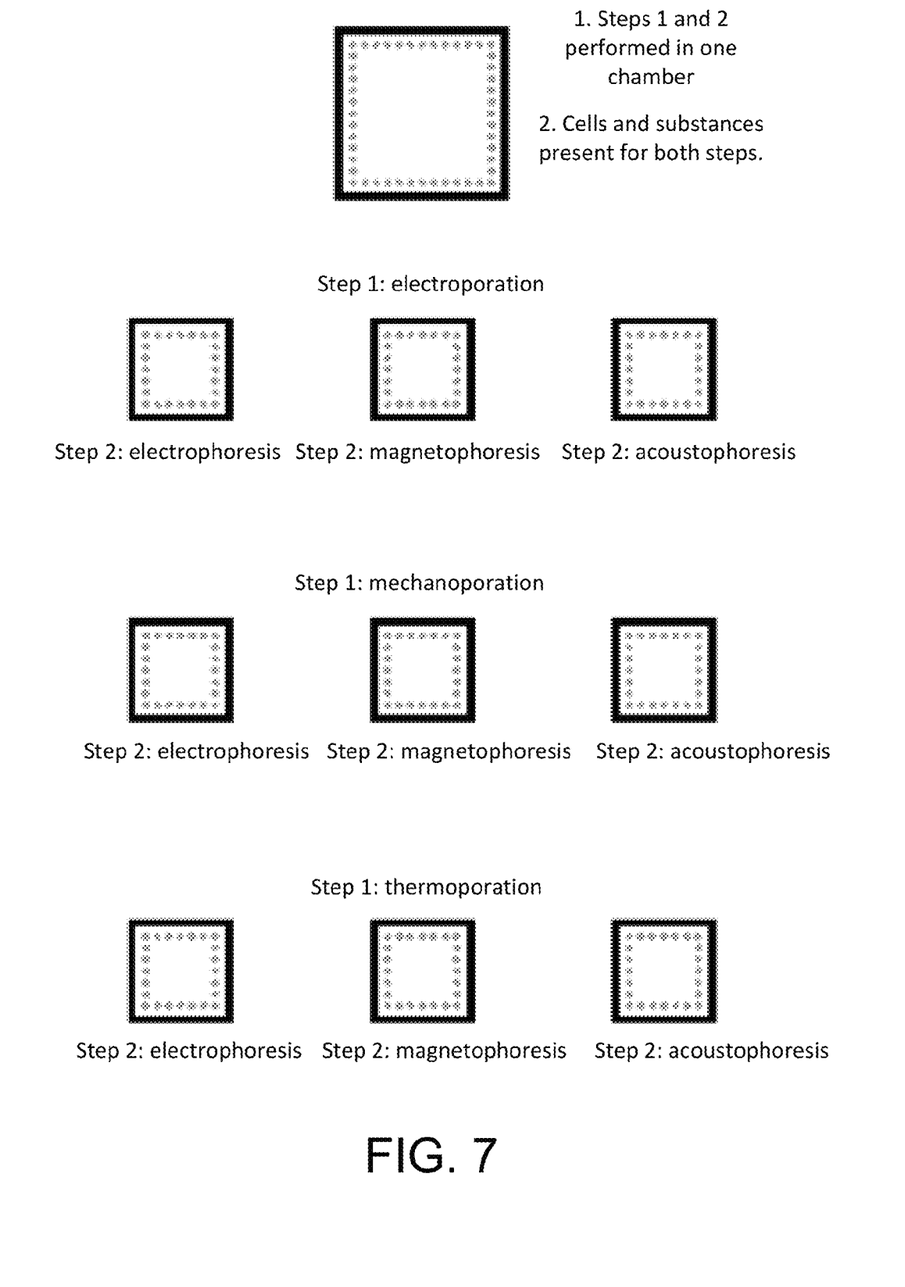
FIG. 7 illustrates various embodiments of the present disclosure.

FIG. 1 is a diagram of the procedure by which cells are treated using these system embodiments. In an embodiment, the device includes a permeabilization system and an insertion system. The first step includes application of an energy field (e.g., an electric, a mechanical, an electromechanical, and thermal, among others) for cell membrane permeabilization, and the second step involves driving and inserting (e.g., electrophoresis, magnetophoresis, an acoustophoresis, and the like) a substance to and into the porated cells through the resultant pores. FIG. 7 includes diagrams over various embodiments of the device with different combinations of permeabilization systems and insertion systems.

Additional steps can include recycling of treated samples (i.e., repetition of steps 1 and 2) to realize better treatment outcomes, sorting of cells, extraction of materials from cells, and other manipulation of cells.

In an embodiment, the permeabilzation system can be performed using techniques selected from a mechanical poration technique, an electrical poration technique, a thermal poration technique, and an electromechanical poration technique, or a combination of two or more of these techniques. In an embodiment, the mechanical poration technique can include an acoustic field generator. In an embodiment, the acoustic field generator can be a tapered passage for focusing acoustic waves or any application of acoustic energy to cells or contrast agents that "react" to the acoustic field either by directly becoming permeabilized or in the case of contrast agents by the cavitation of the contrast agents, which can form a shock wave that disrupts the cell membrane. In another embodiment, the acoustic field generator can include the forced flow of a gas through a passage not much bigger than the cell causing a mechanically shearing of the cell that leads to pore formation. In an embodiment, the electrical poration technique can include a pair or multiple electrodes arranged such that an electric field capable of exceeding the threshold voltage for cell membrane permeabilization is formed. In an embodiment, the thermal poration technique can include microheaters that can rapidly cycle the temperature to which cells are exposed at a cell-scale (in terms of size). In an embodiment, the electromechanical poration technique can include the application of both the electrical and mechanical signals simultaneously, i.e., flowing cells through a small channel with electrodes to shear and electrocute them.

In an embodiment, the insertion system can include: an electrophoretic technique, a magnetophoretic technique, an acoustophoretic technique, and a combination of two or more of these techniques. In an embodiment, the electrophoretic technique can include electrodes (anode(s) and cathode(s)), which generates an electric field capable of inducing motion in charged materials. In an embodiment, the magnetophoretic technique can include magnetic poles (positive and negative), which generates a magnetic field capable of inducing motion in magnetic materials. In an embodiment, the acoustophoretic technique can include one or more transducers that generate an acoustic field capable of inducing motion in materials that possess an appropriate acoustic contrast factor with suspension media.

In an embodiment, the cell can include eukaryotic, prokaryotic, animal, plant, fungi, algae, bacterial, mammalian, primary cells, and stem cells. In an embodiment, the cell can be in a suspension that includes, but is not limited to, cell growth media, electroporation buffer, PBS, and the like. In addition, the suspension includes the substance during poration. In an embodiment, the suspension does not include the substance during poration.

In an embodiment, the substance can include a drug, a charged substance (e.g., biological material), a magnetic substances (e.g., a magnetic nanoparticle that may be attached (e.g., bonded, chelated, etc.) to a substance such a biological material), a substance that moves under the action of an acoustic field (e.g., acoustic contrast agents), or a substance having two or more of a charge, a magnetic characteristic, and an acoustic characteristic. In an embodiment, the biological material can include a polynucleotide, an antigen, a polypeptide, an antibody, a hapten, and an enzyme.

Figure 2:
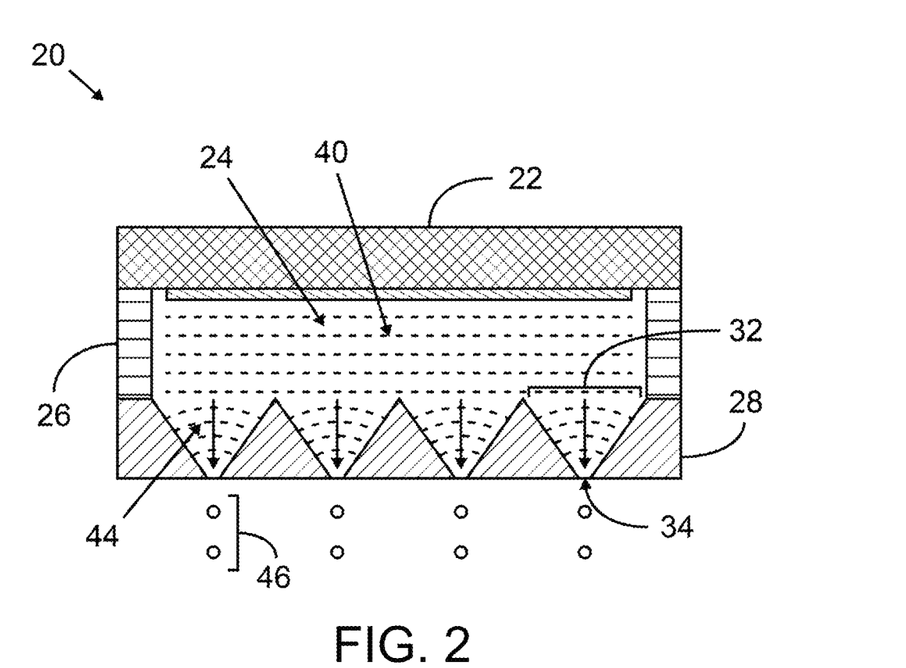
FIG. 2 illustrates a cross-section of an embodiment of a system that can mechanically permeabilize the cell membrane.

FIG. 2 illustrates a cross-section of an embodiment of a system [20] that can mechanically permeabilize the cell membrane. The mechanoporation system [20] includes, but is not limited to, an actuator [22] and an ejection device [28] that form boundaries on two sides of a sample reservoir [24]. The sample reservoir [24] includes the volume of the ejector structures [32]. The ejection device [28] includes, but is not limited to, an array of ejector structures [32] and the ejector orifices [34]. A fluid sample can be disposed in the reservoir [24] and in the ejector structures [32]. Upon actuation of the actuator [22], a resonant ultrasonic wave [40] can be produced within the reservoir [24] and fluid sample. The resonant ultrasonic wave [40] couples to and transmits through the liquid and is focused by the ejector structures [32] to form a pressure gradient [44] within the ejector structures [32]. The high-pressure gradient [44] accelerates fluid out of the ejector structure [32] to produce droplets or a continuous jet of ejected fluid sample [46]. The period of the drive signal applied to the actuator [22] dictates, at least in part, the rate at which fluid sample is ejected.

In general, the material from which the ejector device [28] is made has substantially higher acoustic impedance as compared to the fluid sample. The ejection device [28] can be made of materials such as, but not limited to, single crystal silicon (e.g., oriented in the (100), (010), or (001) direction), metals (e.g., aluminum, copper, and/or brass), plastics, silicon oxide, silicon nitride, and combinations thereof.

The ejector structure [32] can have a shape such as, but not limited to, conical, pyramidal, or horn-shaped with different cross-sections. In general, the cross-sectional area is decreasing (e.g., linear, exponential, or some other functional form) from a base of the ejector structure [32] (broadest point adjacent the reservoir) to the ejector orifice [34] in both two and three dimensions. The cross sections can include, but are not limited to, a triangular cross-section and exponentially narrowing. In an embodiment, the ejector structure [32] is a pyramidal shape. In an embodiment, the ejector structure [32] can be a two dimensional groove terminated by a slot orifice [34] or have a three-dimensional tapered geometry terminated by an arbitrarily-shaped orifice [34] (e.g., circle, square, etc., see below). In another embodiment, geometry of the ejector structure [32] is not tapered, but is terminated by an opening/channel orifice [34] which is of substantially smaller dimension (width or diameter) than the ejector structure [32].

In one embodiment, the ejector structure [32] has acoustic wave focusing properties in order to establish a highly-localized, pressure maximum substantially close to the ejector orifice [34]. This results in a large pressure gradient at the ejector orifice [34] since there is effectively an acoustic pressure release surface at the ejector orifice [34]. Since the acoustic velocity is related to the pressure gradient through Euler's relation, a significant momentum is transferred to the fluid sample volume close to the ejector orifice [34] during each cycle of the acoustic wave in the ejector structure [32]. When the energy coupled by the acoustic wave in the fluid sample volume is substantially larger than the restoring energy due to surface tension, viscous friction, and other sources, the fluid surface is raised from its equilibrium position. Furthermore, the frequency of the waves can be such that there is enough time for the droplet to break away from the surface due to instabilities. Alternatively, the frequency of the waves can be such that the ejection is a continuous jet of the fluid.

The ejector structure [32] has a diameter (at the base of a single structure/nozzle) of about 50 micrometers to 5 millimeters, 300 micrometers to 1 millimeter, and 600 micrometers to 900 micrometers. The distance (height) from the ejector orifice [34] (opening) to the broadest point in the ejector structure [32] (base of the nozzle) is from about 20 micrometers to 4 millimeters, 200 micrometers to 1 millimeter, and 400 micrometers to 600 micrometers.

The ejector orifice [34] size and shape effectively determine the droplet/jet size and the amount of pressure focusing along with the ejector structure [32] geometry (i.e., cavity geometry). The ejector orifice [34] can be formed using various manufacturing techniques as described below and can have a shape such as, but not limited to, circular, polygonal, elliptical, square, rectangle, or rhomboid. The ejector orifice [32] has a diameter of about 50 nanometers to 200 micrometers, 200 nanometers to 100 micrometers, and 1 micrometer to 10 micrometers.

The ejection device [28] can include one ejector structure [32], an (one-dimensional) array of ejector structures [32], or a (two dimensional) matrix of parallel arrays of ejector structures [32]. The ejector structure [32] can include one ejector orifice [34] each or include a plurality of ejector orifices [34] in a single ejector structure [32].

The sample reservoir [24] is substantially defined by the ejection device [28] and the actuator [22], as well as the distance between the two. The other boundaries can be walls [26] or separation layers to contain the fluid sample in the reservoir [24]. The sample reservoir [24] is an open area connected to the open area of the ejector structures [32] such that the fluid sample is in both areas.

In general, the dimensions of the sample reservoir [24] and the ejector structure [32] can be selected to excite a cavity resonance in the structure at a desired frequency. The structures may have cavity resonances of about 20 kHz to 100 MHz, depending, in part, on fluid type and dimensions and cavity shape, when excited by the actuator [22].

The dimensions of the sample reservoir [24] are about 100 micrometers to 4 centimeters in width, about 100 micrometers to 4 centimeters in length, and about 100 nanometers to 5 centimeters in height. In addition, the dimensions of the reservoir [24] are about 100 micrometers to 2 centimeters in width, about 100 micrometers to 2 centimeters in length, and about 1 micrometer to 3 millimeters in height. Further, the dimensions of the reservoir [24] are about 100 micrometers to 1 centimeter in width, about 100 micrometers to 1 centimeter in length, and about 100 micrometers to 2 millimeters in height.

The actuator [22] produces a resonant ultrasonic wave [40] within the reservoir [24] and fluid sample. As mentioned above, the resonant ultrasonic wave [40] couples to and transmits through the liquid and is focused by the ejector structures [32] to form a pressure gradient within the ejector structure [32]. If the orifices [34] are open for ejection, the high-pressure gradient accelerates fluid out of the orifices

[34] from the ejector structure [32] to produce ejection. Ejection can produce discrete droplets in a drop-on-demand manner or a continuous jet. The frequency at which the droplets are formed is a function of the drive wave form applied to the actuator [22] as well as the fluid, reservoir [24], ejector structure [32], and the ejector orifice [34].

Different actuators can be used to drive the self-pumping device and also to produce fluid ejection, including the piezoelectric and capacitive type (e.g., CMUT). An alternating voltage is applied to the actuator [22] to cause the actuator [22] to produce the resonant ultrasonic wave [40]. The actuator [22] can operate at about 20 kHz to 100 MHz, about 500 kHz to 15 MHz, and about 800 kHz to 5 MHz. A direct current (DC) bias voltage can also be applied to the actuator [22] in addition to the alternating voltage. In embodiments where the actuator [22] is piezoelectric, this bias voltage can be used to prevent depolarization of the actuator [22] and also to generate an optimum ambient pressure in the reservoir. In embodiments where the actuator [22] is electrostatic, the bias voltage is needed for efficient and linear operation of the actuator [22]. Operation of the actuator [22] is optimized within these frequency ranges in order to match the cavity resonances, and depends on the dimensions of and the materials used for fabrication of the sample reservoir [24] and the ejection device [28] as well the acoustic properties of the fluid sample.

The actuator [22] can include, but is not limited to, a piezoelectric actuator and a capacitive actuator. The piezoelectric actuator and the capacitive actuator are described in X. C. Jin, I. Ladabaum, F. L. Degertekin, S. Calmes and B. T. Khuri-Yakub, "Fabrication and Characterization of Surface Micromachined Capacitive Ultrasonic Immersion Transducers", IEEE/ASME Journal of Microelectromechanical Systems, 8, pp. 100-114 (1999) and Meacham, J. M., Ejimofor, C., Kumar, S., Degertekin F. L., and Fedorov, A., "A Micromachined Ultrasonic Droplet Generator Based on Liquid Horn Structure", Rev. Sci. Instrum., 75 (5), 1347-1352 (2004), which are incorporated herein by reference.

One particular embodiment that enables low power input ejection of the fluid is resonant, ultrasonically driven atomization which operates by providing an AC electrical signal to the actuator [22] (piezoelectric transducer) with a frequency equal to the resonance of the fluid filled cavity (sample reservoir [24] and set of ejector structures [32]). The resonant acoustic wave [40] in the fluid in the sample reservoir [24] is focused by the ejector structures [32] (e.g., pyramidal nozzles), creating a high pressure gradient at the ejector structure orifice [34], and thus ejecting the fluid that fills the nozzle cavity. Since the ejector structures [32] can be fabricated using micromachining techniques the orifice [34] size is well controlled, resulting in monodisperse droplet ejection for precise flow rate control. Additional details regarding ultrasonically driven atomization are described in publications (Meacham, J. M., Ejimofor, C., Kumar, S., Degertekin F. L., and Fedorov, A., 2004, "A Micromachined Ultrasonic Droplet Generator Based on Liquid Horn Structure", Review of Scientific Instruments, Vol. 75, No. 5, pp. 1347-1352; Meacham, J. M., Varady, M., Degertekin F. L., and Fedorov, A., 2005, "Droplet Formation and Ejection from a Micromachined Ultrasonic Droplet Generator: Visualization and Scaling", Physics of Fluids, Vol. 17, No. 10, pp. 100605-100613; Meacham, J. M., Varady, M., Esposito, D., Degertekin, F. L., and Fedorov, A., "A Micromachined Ultrasonic Atomizer For Liquid Fuels", Atomization and Sprays, 18, pp. 163-190 (2008)), each of which is incorporated herein by reference.

The dimensions of the actuator [22] depend on the type of actuator used. For embodiments where the actuator [22] is a piezoelectric actuator, the thickness of the actuator [22] is determined, at least in part, by the frequency of operation and the type of the piezoelectric material. The thickness of the piezoelectric actuator is chosen such that the thickness of the actuator [22] is about half the wavelength of longitudinal waves in the piezoelectric material at the frequency of operation. Therefore, in case of a piezoelectric actuator, the dimensions of the actuator [22] are about 100 micrometers to 10 centimeters in width, about 10 micrometers to 1 centimeter in thickness, and about 100 micrometers to 10 centimeters in length. In addition, the dimensions of the actuator [22] are about 100 micrometers to 2 centimeters in width, about 10 micrometers to 5 millimeters in thickness, and about 100 micrometers to 2 centimeters in length. Further, the dimensions of the actuator [22] are about 100 micrometers to 1 centimeter in width, about 10 micrometers to 2 millimeters in thickness, and about 100 micrometers to 1 centimeter in length.

In embodiments where the actuator [22] is a capacitive actuator, the actuator [22] is built on a wafer made of silicon, glass, quartz, or other substrates suitable for microfabrication, where these substrates determine the overall thickness of the actuator [22]. Therefore, in case of a capacitive microfabricated ultrasonic transducer (CMUT) and CMUT arrays, the dimensions of the actuator [22] are about 10 micrometers to 4 centimeters in width, about 10 micrometers to 2 millimeter in thickness, and about 10 micrometers to 4 centimeters in length. In addition, the dimensions of the actuator [22] are about 100 micrometers to 2 centimeters in width, about 10 micrometers to 1 millimeter in thickness, and about 100 micrometers to 2 centimeters in length. Further, the dimensions of the actuator [22] are about 100 micrometers to 1 centimeter in width, about 10 micrometers to 600 micrometers in thickness, and about 100 micrometers to 1 centimeter in length.

The fluid sample can be liquids such as, but not limited to, water, methanol, dielectric fluorocarbon fluid, organic solvent, cell culture media, buffer solutions, electroporation buffers, or other liquids, and combinations thereof. Fluid samples can also include suspensions of biological cells and/or one or more other materials, including but not limited to, drug molecules, nucleic acids, imaging agents, peptides, antibodies, enzymes, and other nanomaterials and biomolecules.

If the fluid sample contains biological cells, ejection from the orifices [34] of the ejection device [28] provides a mechanical shear force that induces a tension in the cell membranes. Provided the induced membrane tension exceeds a certain threshold value, cells can be either reversibly porated for cargo molecule delivery or irreversibly porated leading to eventual cell death or immediate cell lysis.

As mentioned above, the embodiments described thus far represent one system, and method, which is capable of permeabilizing the membranes of living cells. In general, other poration methods (e.g., electric, mechanical, electromechanical, and thermal, among others) could be used to achieve membrane permeabilization and provide step 1 of the multistage procedure that is the subject of the present disclosure. Here, embodiments of the present disclosure that provide a means of actively driving and inserting DNA or other biological material to and into porated cells (step 2 of the multistage procedure) are described.

Figure 3:
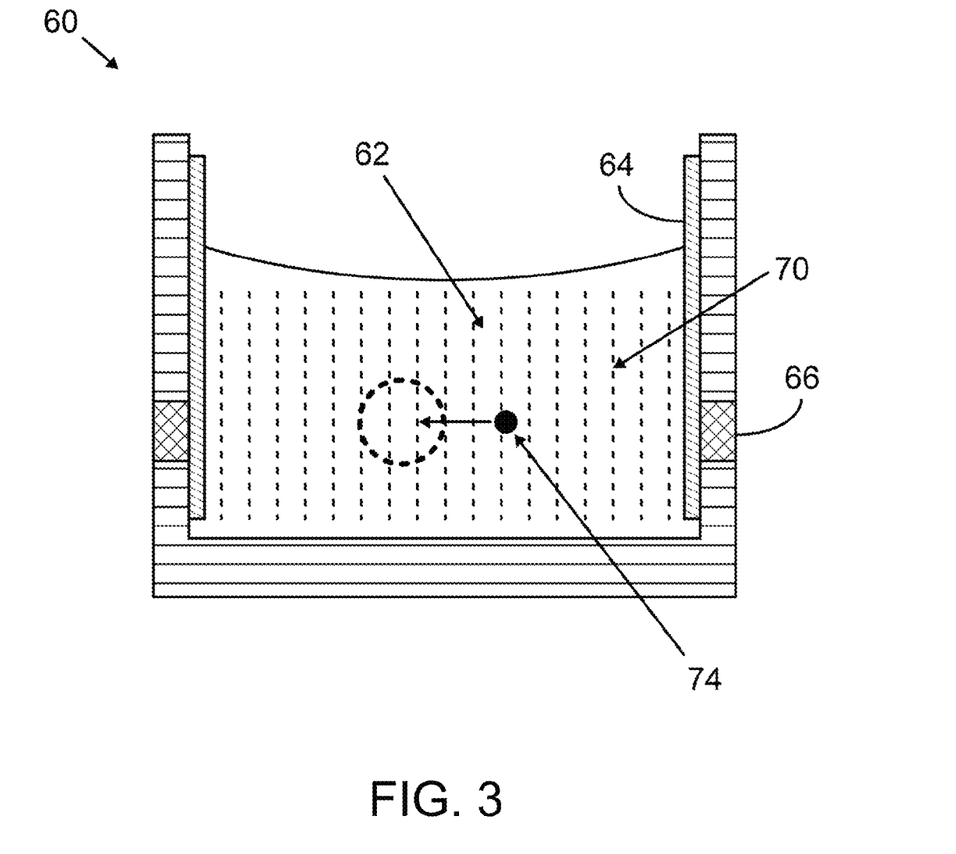
FIG. 3 illustrates an embodiment of a cuvette that can be used for electrophoresis.

FIG. 3 illustrates a cross-section of an embodiment of an insertion system [60] that can actively drive charged materials (e.g., DNA or other biomolecules, among other materials) to and into porated cells. The electrophoresis system [60] includes, but is not limited to, a collection/treatment reservoir [62] and electrodes [64] that form boundaries on two or more sides of the collection reservoir [62]. Each electrode [64] is electrically coupled to an electrical contact [66]. Fluid sample can be collected in the reservoir [62] after ejection from the orifices [34] of the ejection device [28]. Upon application of an electric potential difference on the electrical contacts [66], an electric field [70] is generated between the electrodes [64] within the reservoir [62]. This field acts on charged materials [74] within the fluid sample causing them to move. For example, negatively charged DNA molecules would move in a direction away from a negative cathode and toward a positive anode. If the fluid sample in the reservoir [62] contains porated biological cells, the charged materials will move to and into the interior of the cells through the pores. Further, the cell surface area over which charged materials can enter the cells through the porated cell membrane can be increased by changing the polarity and orientation of the electric field, e.g., by modulating the voltage signal applied to the electrophoresis electrodes.

In the embodiment shown in FIG. 3, two electrodes [64] are placed opposite one another on either side of the collection reservoir [62]. The distance between electrodes [64] can be about 50 micrometers to 10 millimeters. In addition, the distance between electrodes [64] can be about 250 micrometers to 5 millimeters. Further, the distance between electrodes [64] can be about 1 millimeters to 2 millimeters. In this embodiment, the reservoir [62] is substantially defined by the width, height, and the distance between the electrodes [64]. The width of the electrodes [64] can be about 50 micrometers to 10 centimeters. In addition, the width of the electrodes [64] can be about 500 micrometers to 5 centimeters. Further, the width of the electrodes [64] can be about 5 millimeters to 1 centimeter. The height of the electrodes [64] can be about 50 micrometers to 10 centimeters. In addition, the height of the electrodes [64] can be about 500 micrometers to 5 centimeters. Further, the height of the electrodes [64] can be about 5 millimeters to 1 centimeter. The collected volume can be 100 picoliters to 100 milliliters. In addition, the collected volume can be 100 nanoliters to 10 milliliters. Further, the collected volume can be 100 microliters to 1 milliliter. The volume of fluid sample in the reservoir [62] dictates the liquid height within the reservoir [62].

The electrode [64] can include, but is not limited to, aluminum, other metals, or conductive polymers. For parallel electrodes, the electric field strength E is dependent upon the voltage V applied to the electrodes [64] and the distance d between the electrodes [64] as $E=V/d$. The voltage is applied such that the electric field strength can be about 0.001 volts to 1 kilovolt per centimeter. In addition the electric field strength can be about 10 and 500 volts per centimeter. Further, the electric field strength can be about 50 and 100 volts per centimeter. This value is dramatically lower than the field strength required to permeabilize typical biological cells through electroporation, i.e., a typical threshold field strength of greater than 1 kilovolt per centimeter.

As mentioned above, the polarity and orientation of the electric field can be modulated to improve delivery of charged materials to and into cells by increasing the cell surface area over which charged materials can enter the pores of permeabilized cells. Electrodes can be oriented on two or more sides of an arbitrarily shaped (e.g., square, rectangular, polygonal, or circular, among others) collection reservoir [62]. An alternating (AC) or direct current (DC) voltage can be applied to one or more electrodes to fix or arbitrarily vary the polarity and orientation of the electric field in a reservoir [62]. Along with the voltage amplitude, modulation of the polarity and orientation of the electric field can be used to control the motion of charged materials (direction and velocity of movement).

As described herein, the methods and systems provide for a cell membrane permeabilization (or permeabilization of cell like structures such as a virus, a virus like particle, a vesicle, and other nano- and microstructures defined by a membrane) followed by driving and inserting substances (e.g., molecules, charged molecules, and the like such as DNA, RNA, or other biological material or molecules) to and into the porated cells through the resultant pores formed during permeabilization.

Embodiments of the device can be assembled such that the steps of cell membrane permeabilization and driving and inserting substances to and into the porated cells through the resultant pores comprise a single device structure or two or more device structures housing the necessary components to achieve single- or multi-mode permeabilization and single- or multi-mode material insertion.

Embodiments assembled as a single device could include an injection molded plastic cartridge containing embedded actuators (including a piezoelectric actuator for driving ejection from the ejection device and electrodes for applying the field needed for electrophoresis of charged molecules, among others), embedded ejection devices, and fluidic channels and reservoirs, among other components.

Embodiments that have separate components could include a separate piezoelectric actuator module that is coupled to other components using an acoustic coupling layer. The resonant ultrasonic wave couples to and transmits through the acoustic coupling layer from the piezoelectric actuator into the sample reservoir. The dimensions of the acoustic coupling layer depend on the speed of sound characteristic of its material of construction. The thickness of the acoustic coupling layer is chosen such that the thickness of the acoustic coupling layer is about half the wavelength of longitudinal waves in the acoustic coupling layer at the frequency of operation. Therefore, in case of an aluminum acoustic coupling layer, the dimensions of the acoustic coupling layer are about 100 micrometers to 10 centimeters in width, about 10 micrometers to 1 centimeter in thickness, and about 100 micrometers to 10 centimeters in length. In addition, the dimensions of the acoustic coupling layer are about 100 micrometers to 2 centimeters in width, about 10 micrometers to 5 millimeters in thickness, and about 100 micrometers to 2 centimeters in length. Further, the dimensions of the acoustic coupling layer are about 100 micrometers to 1 centimeter in width, about 10 micrometers to 2 millimeters in thickness, and about 100 micrometers to 1 centimeter in length. The acoustic coupling layer material can be metal, silicon, glass, or combinations of these, among other materials.

Thus, using embodiments of the systems described herein, an energy field (e.g., electric, mechanical, electromechanical, and thermal, among others) can be applied to cause cell membrane permeabilization. Subsequently, a charge molecule such as DNA can be driven and inserted to and into the porated cells through the resultant pores.

Embodiments of the present disclosure can be used to individually control the delivery and transfection on a single-cell level. Embodiments of the present disclosure can be used to simultaneously size-sort transfected cells. In an embodiment, the device and method can be used for high-throughput and multiplexed operation in microarray format. Small sample volumes can be used. Embodiments can be used in both continuous and discrete operation.

Characterization experiments have demonstrated capabilities of embodiments of the present disclosure and these include: controllable array operation in drop-on-demand (DOD) and continuous-jetting modes for high-efficiency intracellular delivery and transfection; low power (<100 milli-Watts) and temperature (<30° C.) sample ejection without device clogging by cells/biomolecules and with proven thermal stability of operation; flow cytometry and fluorescence microscopy results that unambiguously indicate that biological cells remain alive after processing in both the mechanoporation/diffusive uptake and combined mechanoporation/active electrophoresis delivery modes of operation; flow cytometry and fluorescence microscopy results that unambiguously indicate that biological cells are able to uptake foreign molecules (e.g., fluorescent markers such as green fluorescent calcein dye and FITC-labeled dextran, which do not penetrate the cell membrane under normal conditions) from the surrounding environment upon ejection by the Electrosonic Cell Manipulation Device; and Flow cytometry and fluorescence microscopy results that unambiguously indicate that transfection of DNA plasmid encoding GFP is significantly enhanced through use of combined mechanoporation using the Electrosonic Cell Manipulation Device and subsequent application of a low-amplitude electric field for DNA electrophoresis to and into cells.

While embodiments of the present disclosure are described in connection with the Examples and the corresponding text and figures, there is no intent to limit the invention to the embodiments in these descriptions. On the contrary, the intent is to cover all alternatives, modifications, and equivalents included within the spirit and scope of embodiments of the present disclosure.

Example 1

Figure 4:
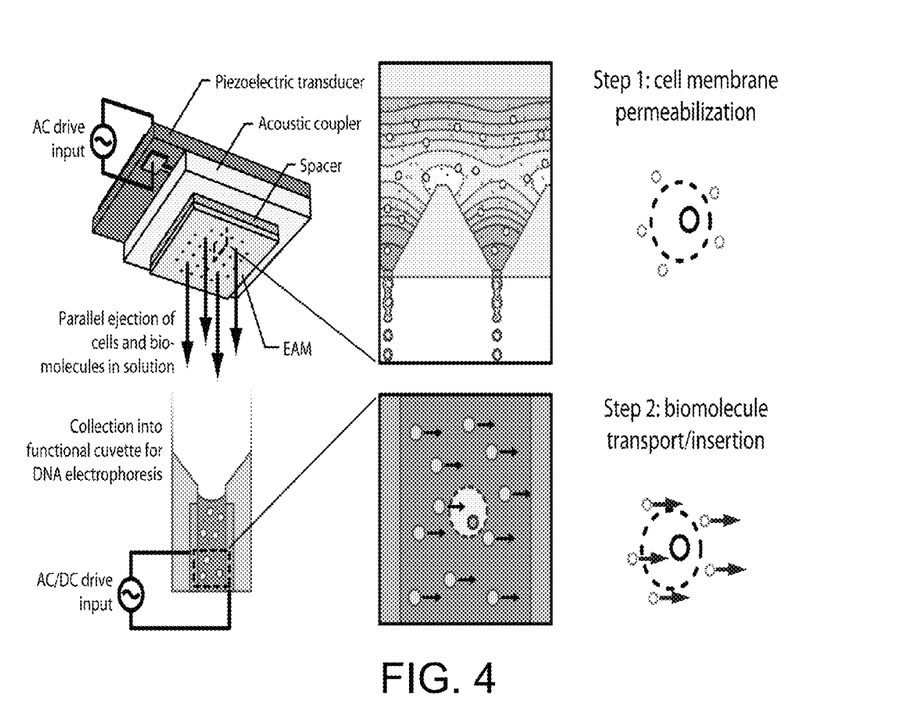
FIG. 4 illustrates an embodiment of a system that incorporates the electrostatic cell manipulation device.

Large Molecule Delivery Via Mechanoporation Using the Electrosonic Cell Manipulation Device An exemplary embodiment of a mechanoporation system (incorporating an actuator and ejection device) termed the Electrosonic Cell Manipulation Device is shown in FIG. 4. As shown in FIG. 4, the mechanoporation system includes a piezoelectric transducer, a fluid reservoir, and a silicon cover plate containing the micromachined ejector nozzles, similar to the design in FIG. 2. A PZT-8 ceramic is selected for the piezoelectric transducer. The device generates droplets or jets by utilizing cavity resonances in the about 0.5 to 5 megahertz range, along with the acoustic wave focusing properties of liquid horns formed by a silicon wet etching process. Anisotropic wet etching of (100) oriented single crystal silicon yields a pyramidal nozzle shape, which is suitable for focusing acoustic waves. At resonance, a standing acoustic wave is formed in the fluid sample reservoir with the peak pressure gradient occurring at the tip of the nozzle leading to ejection. Finite element analysis using ANSYS not only confirms the acoustic wave focusing by the horn structure shown in FIG. 4, but also accurately predicts the resonant frequencies at which the device provides stable ejection (Meacham, J. M., Ejimofor, C., Kumar, S., Degertekin F. L., and Fedorov, A., 2004, "A Micromachined Ultrasonic Droplet Generator Based on Liquid Horn Structure", Review of Scientific Instruments, Vol. 75, No. 5, pp. 1347-1352; Meacham, J. M., Varady, M., Degertekin F. L., and Fedorov, A., 2005, "Droplet Formation and Ejection from a Micromachined Ultrasonic Droplet Generator Visualization and Scaling", Physics of Fluids, Vol. 17, No. 10, pp. 100605-100613; Meacham, J. M., Varady, M., Esposito, D., Degertekin, F. L., and Fedorov, A., "A Micromachined Ultrasonic Atomizer For Liquid Fuels", Atomization and Sprays, 18, pp. 163-190 (2008)).

The Electrosonic Cell Manipulation Device shown in FIG. 4 can be used for biological cell manipulation such as lysis (disruption of a cell membrane and removal of material from the cell), poration (reversibly opening pores in a cell membrane to enable material transfer into and out of the cell), transfection (transfer of genetic material into the cell), and sorting. As described above, when biological cells suspended in the fluid sample are ejected from the orifices [34] of the ejection device [28], a mechanical shear force induces a tension in the cell membranes. When this induced membrane tension exceeds a certain threshold value, cells can be reversibly porated for cargo molecule delivery (e.g., DNA). For reversible cell membrane permeabilization and delivery of foreign materials, ejector orifice diameters ranging from ~30 micrometers to ~60 micrometers are found to provide optimal treatment of mammalian cells ranging in diameter from ~5 micrometers to ~25 micrometers, i.e., poration of the cell membrane under these treatment conditions allows some of the material in suspension with the cells to pass into the cells. Successful delivery of the small molecule calcein has been achieved in a number of cell types (LN443, HEK293, DU145, Jurkat, K562 and primary monocytes) to establish baseline capabilities of our delivery method.

The Electrosonic Cell Manipulation Device is realized by incorporating silicon ejector microarrays into prototype cell treatment cartridges that included a sample reservoir, inlet/relief ports, and fluidic channels. These cartridges were outfitted with 32-nozzle microarrays with orifice diameters ranging from about 10 to 70 micrometers. To prepare for an experiment, the reservoir of a cartridge was loaded with about 750 microliters of sample mixture. The sample mixture included biological cells, uptake materials such as fluorescently labeled biomolecules or DNA, and complete growth media that is specific to a given cell type. To avoid overheating of the piezoelectric transducer, a pulsing waveform was used with an approximately 50% duty cycle (50,000 cycles on and 50,000 cycles off) and a driving frequency between 1.1 and 1.3 megahertz.

Figure 5:
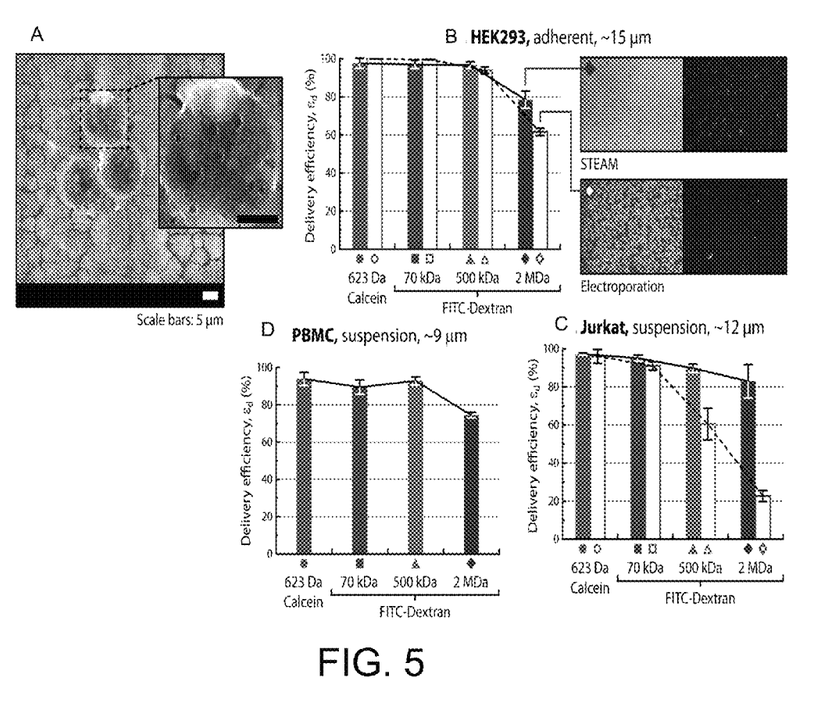
FIG. 5 illustrates EAM membrane permeabilization and large molecule delivery.

The Electrosonic Cell Manipulation Device has demonstrated an ability to overcome cargo size limitations inherent in other intracellular delivery methods. As shown in FIG. 5A, SEM images of HEK293 cells (adherent, about 15 micrometer diameter) immediately after ejection from a cartridge with 40 micrometer orifices suggest that some pores are 100 s of nanometers in diameter, significantly larger than the largest electropores (about 20-50 nanometer diameter) reported in the literature [Meacham, J. M., Durvasula, K., Degertekin, F. L., and Fedorov, A. G., 2013, "Physical Methods for Intracellular Delivery: Practical Aspects from Laboratory Use to Industrial-Scale Processing," Journal of Laboratory Automation, Online First Jun. 27, 2013; Krassowska, W., and Filev, P. D., 2007, "Modeling electroporation in a single cell," Biophysical Journal, 92(2), pp. 404-417; Lechardeur, D., Verkman, A. S., and Lukacs, G. L., 2005, "Intracellular routing of plasmid DNA during non-viral gene transfer," Advanced Drug Delivery Reviews, 57(5), pp. 755-767.]. A direct comparison of mechanoporation using an Electrosonic Cell Manipulation Device and electroporation-mediated delivery efficiency (as a function of cargo molecule size) for two laboratory-established cell lines has provided additional validation of this observation (see FIGS. 5B and 5C). For the largest cargo molecule (2 mega-Dalton FITC-labeled dextran) investigated, mechanoporation-mediated delivery using an Electrosonic Cell Manipulation Device is approximately 25% more efficient using the relatively 'easy-to-transfect' HEK293 cell line. Further, fluorescence microscopy indicates that the Electrosonic Cell Manipulation Device loads significantly more molecules into each individual cell. For the more difficult-to-transfect Jurkat cell line (suspension, about 12 micrometer diameter), the performance improvement is more pronounced as the Electrosonic Cell Manipulation Device achieves a four-fold increase in delivery efficiency of 2 mega-Dalton FITC-dextran compared to electroporation. Critically, high delivery efficiency (>74%) is maintained even for delivery of 2 mega-Dalton FITC-dextran into extremely difficult-to-transfect primary monocytes (peripheral blood mononuclear cells, PBMCs, suspension, about 9 micrometer diameter) (see FIG. 5D). Cell viability assessed using nuclear-membrane staining propidium iodide was greater than 90% for all cases. All cells were suspended in complete growth media for treatment.

Example 2

Plasmid DNA Transfection Via Combined Mechanoporation/Electrophoresis

DNA transfection is inherently more challenging than biomolecule delivery into the cytoplasm. In addition to crossing the cell membrane, DNA must reach and enter the cell nucleus intact. The degree to which gene transfer is impeded is cell-type dependent, and the factors that influence these processes are not well-understood [Lechardeur, D.; Lukacs, G. L., Intracellular barriers to non-viral gene transfer. Curr. Gene Ther. 2002, 2 (2), 183-194; Lechardeur, D.; Verkman, A. S.; Lukacs, G. L., Intracellular routing of plasmid DNA during non-viral gene transfer. Adv. Drug Deliv. Rev. 2005, 57 (5), 755-767; Belting, M.; Sandgren, S.; Wittrup, A., Nuclear delivery of macromolecules: Barriers and carriers. Adv. Drug Deliv. Rev. 2005, 57 (4), 505-527.]. While no physical method of delivery is able to completely eliminate all barriers to transfection, the multistage procedure for treatment of biological samples described in the present disclosure has demonstrated an ability to significantly improve transfection outcomes over those that only rely on the Electrosonic Cell Manipulation Device and passive uptake by diffusion.

Figure 6:
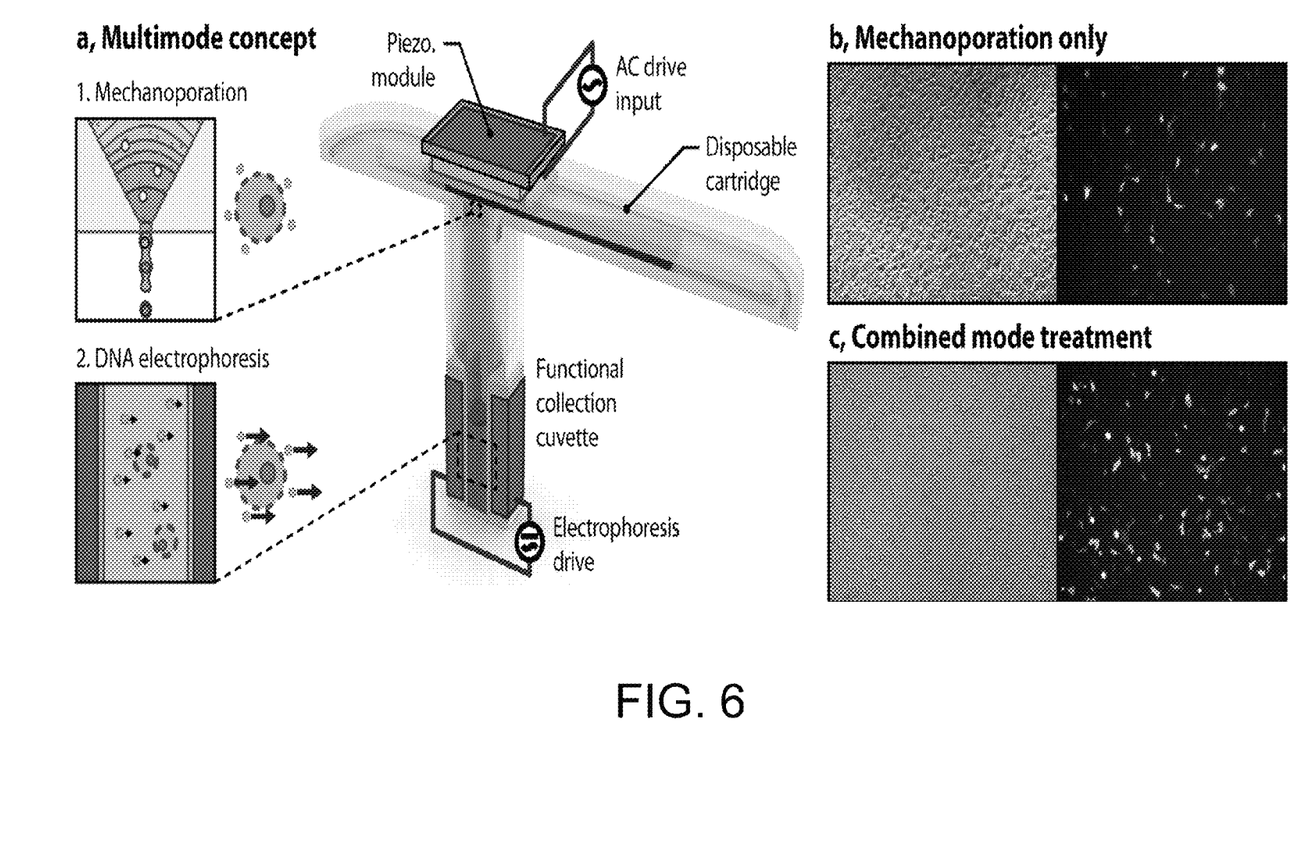
FIG. 6 illustrates the combined mode of transfection.

The microcentrifuge tube that was used to collect sample for large molecule uptake experiments was replaced by an electroporation cuvette with a 4 millimeter gap (see FIG. 6). A nearly two-fold increase in transfection efficiency has been achieved by applying a low strength electric field to mechanically porated HEK293 and Jurkat cells within 10 s of seconds of mechanoporation and collection into the electroporation cuvette. FIGS. 6B and 6C show an increase in expression of green fluorescent protein (GFP) from 50% to 91% for HEK293 cells (2 million cells per milliliter) transfected with DNA plasmid encoding GFP (50 microgram per milliliter) after applying a 75 volt per centimeter field to collected mechanoporated cells for 500 microseconds. Transfection experiments were performed on cells suspended in complete growth media.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

We claim:

1. A method of delivering a substance into a living cell having a cell membrane, comprising:
a) permeabilization of the cell membrane in a suspension to form pores in the cells using a permeabilization system, and
b) actively transporting and incorporating a substance into the cell interior through pores formed during permeabilization of the membrane using an insertion system.

2. The method of claim 1, wherein permeabilization includes permeabilization of the cell membrane using a technique selected from the group consisting of: mechanical poration, electrical poration, thermal poration, and a combination of two or more of these techniques.

3. The method of claim 2, wherein the mechanical poration includes poration using an acoustic field, an action of a shear field, or a combination of an acoustic field and a shear field.

4. The method of claim 1, wherein the transporting and incorporating is conducted using an energetic technique selected from the group consisting of: an electrophoretic technique, a magnetophoretic technique, an acoustophoretic technique, and a combination of two or more of these techniques.

5. The method of claim 1, wherein the transporting and incorporating includes delivering the substance to the cell interior.

6. The method of claim 1, wherein the transporting and incorporating includes delivering the substance to a subcellular target.

7. The method of claim 6, wherein delivery includes delivering the substance to the nucleus or mitochondria.

8. The method of claim 1, wherein permeabilization is conducted on a cell suspension that does not include the substance.

9. The method of claim 8, wherein the substance is added to the cell suspension during step b).

10. The method of claim 1, wherein steps a) and b) are performed sequentially in a single chamber.

11. The method of claim 1, wherein steps a) and b) are performed separately.

12. The method of claim 1, wherein the substance is selected from the group consisting of: a charged substance, a magnetic substance, a substance that moves under the action of an acoustic field, and a combination of two or more of these.

13. The method of claim 12, wherein the charged substance is selected from the group consisting of: a drug, a polynucleotide, an antigen, a polypeptide, an antibody, an antigen, a hapten, and an enzyme.

14. The method of claim 13, wherein the magnetic substance is a magnetic nanoparticle.

15. The method of claim 14, wherein the magnetic nanoparticle is attached to a substance selected from the group consisting of: a drug, a polynucleotide, an antigen, a polypeptide, an antibody, an antigen, a hapten, and an enzyme.

16. The method of claim 1, wherein transporting and incorporating includes applying an electric field of about 0.001 volts to 1 kilovolt per centimeter to the suspension.

17. The method of claim 1, wherein transporting and incorporating includes applying an electric field of about 50 volts to 100 volt per centimeter to the suspension.

\* \* \* \* \*